(12) United States Patent
Schon

(10) Patent No.: US 8,708,956 B2
(45) Date of Patent: Apr. 29, 2014

(54) MULTI-LUMEN CATHETER WITH PROTECTED TIP

(75) Inventor: Donald A. Schon, Paradise Valley, AZ (US)

(73) Assignee: TwinCath LLC, Paradise Valley, AZ (US)

(*) Notice: Subject to any disclaimer, the term of this patent is extended or adjusted under 35 U.S.C. 154(b) by 0 days.

(21) Appl. No.: 13/252,321

(22) Filed: Oct. 4, 2011

(65) Prior Publication Data

US 2012/0022501 A1 Jan. 26, 2012

Related U.S. Application Data

(63) Continuation of application No. 11/807,105, filed on May 25, 2007.

(60) Provisional application No. 60/810,998, filed on Jun. 5, 2006.

(51) Int. Cl.
*A61M 29/00* (2006.01)
*A61M 31/00* (2006.01)
*A61M 25/00* (2006.01)

(52) U.S. Cl.
USPC ............................ 604/104; 604/509; 604/523

(58) Field of Classification Search
USPC ........ 604/29, 43, 96.01, 102.01–102.03, 523, 604/104, 509
See application file for complete search history.

(56) References Cited

U.S. PATENT DOCUMENTS

| | | | |
|---|---|---|---|
| 3,807,408 A | 4/1974 | Summers | |
| 4,211,233 A | 7/1980 | Lin | |
| 4,540,402 A | 9/1985 | Aigner | |
| 4,543,087 A | 9/1985 | Sommercorn et al. | |
| 4,842,583 A | 6/1989 | Majlessi | |
| 5,059,177 A * | 10/1991 | Towne et al. | 604/102.02 |
| 5,087,246 A * | 2/1992 | Smith | 604/103.13 |
| 5,167,239 A * | 12/1992 | Cohen et al. | 600/585 |
| 5,169,378 A * | 12/1992 | Figuera | 600/16 |
| 5,209,723 A * | 5/1993 | Twardowski et al. | 604/43 |
| 5,290,247 A | 3/1994 | Crittenden | |

(Continued)

OTHER PUBLICATIONS

International Preliminary Report dated Sep. 9, 2008; PCT/US07/12487 (3 pages).

(Continued)

*Primary Examiner* — Kevin C Sirmons
*Assistant Examiner* — William Carpenter
(74) *Attorney, Agent, or Firm* — Glenn M. Massina, Esq.; Fox Rothschild LLP

(57) ABSTRACT

A multilumen catheter assembly including an elongated body defining a first lumen having a sidewall extending between its proximal end and a first lumen distal end proximate the body distal end and a first distal opening disposed proximate the first lumen distal end, and a second lumen connected to the sidewall and extending between the proximal end and a second lumen distal end proximate the body distal end, the second lumen distal end distal of the first lumen distal end. The second lumen includes a second distal opening disposed distally of the first distal opening. A self-expanding protector adjoins the elongate body distally of the first distal opening and extends from an inner edge along the elongate body outwardly and proximally to a free proximal edge that extends circumferentially about the elongate body proximate the first distal opening. The protector defins through-ways that permit blood flow past the protector.

20 Claims, 4 Drawing Sheets

(56) References Cited

U.S. PATENT DOCUMENTS

| | | | |
|---|---|---|---|
| 5,295,995 A * | 3/1994 | Kleiman | 606/194 |
| 5,405,320 A | 4/1995 | Twardowski et al. | |
| 5,458,572 A * | 10/1995 | Campbell et al. | 604/103.08 |
| 5,545,132 A * | 8/1996 | Fagan et al. | 604/103.08 |
| 5,693,014 A * | 12/1997 | Abele et al. | 604/103.08 |
| 5,792,300 A * | 8/1998 | Inderbitzen et al. | 156/244.13 |
| 5,807,329 A * | 9/1998 | Gelman | 604/102.03 |
| 6,007,517 A * | 12/1999 | Anderson | 604/103.04 |
| 6,179,859 B1 * | 1/2001 | Bates et al. | 606/200 |
| 6,280,423 B1 | 8/2001 | Davey et al. | |
| 6,371,969 B1 | 4/2002 | Tsugita et al. | |
| 6,394,978 B1 * | 5/2002 | Boyle et al. | 604/103.06 |
| 6,398,758 B1 | 6/2002 | Jacobsen et al. | |
| 6,595,966 B2 | 7/2003 | Davey et al. | |
| 6,632,196 B1 * | 10/2003 | Houser | 604/96.01 |
| 6,709,415 B2 | 3/2004 | Navia et al. | |
| 6,786,884 B1 | 9/2004 | DeCant, Jr. et al. | |
| 6,814,718 B2 * | 11/2004 | McGuckin et al. | 604/264 |
| 6,991,625 B1 * | 1/2006 | Gately et al. | 604/523 |
| 7,004,963 B2 * | 2/2006 | Wang et al. | 623/1.11 |
| 7,077,829 B2 * | 7/2006 | McGuckin et al. | 604/264 |
| 7,252,675 B2 | 8/2007 | Denison et al. | |
| 7,335,023 B2 | 2/2008 | Mahlmann | |
| 8,114,049 B2 * | 2/2012 | Freyman et al. | 604/103.08 |
| 2004/0064090 A1 * | 4/2004 | Keren et al. | 604/96.01 |
| 2004/0167463 A1 | 8/2004 | Zawacki et al. | |
| 2004/0193103 A1 | 9/2004 | Kumar | |
| 2004/0193108 A1 * | 9/2004 | Ackerman et al. | 604/103.07 |
| 2005/0203568 A1 * | 9/2005 | Burg et al. | 606/200 |

OTHER PUBLICATIONS

International Search Report date May 19, 2008; PCT Application No. PCT/US07/12487.

Written Opinion dated May 19, 2008; PCT Application No. PCT/US07/12487 (4 pages).

* cited by examiner

MULTI-LUMEN CATHETER WITH PROTECTED TIP

CROSS-REFERENCE TO RELATED APPLICATIONS

This application is a Continuation application of U.S. patent application Ser. No. 11/807,105 filed May 25, 2007, which claims the benefit of U.S. Provisional Application Ser. No. 60/810,998 filed Jun. 5, 2006.

FIELD OF THE INVENTION

The present invention relates to a multi-lumen catheter assembly used to simultaneously withdraw and infuse a fluid to a body, such as during hemodialysis.

BACKGROUND OF THE INVENTION

Catheters for the introduction or removal of fluids may be placed in various venous locations and cavities throughout the body for introduction or removal of these fluids. Such catheterization may be performed by using a single catheter assembly having multiple lumens. A typical example of a multiple lumen catheter assembly is a dual lumen catheter in which one lumen introduces fluid and the other lumen removes fluid. Such a multiple lumen catheter assembly is known as the SPLIT STREAM® catheter, manufactured and sold by Medical Components, Inc. of Harleysville, Pa.

Generally, to insert any catheter into a blood vessel, the vessel is identified by aspiration through a long hollow needle in accordance with the well known Seldinger technique. When blood enters a syringe attached to the needle, indicating that the vessel has been found, a thin guide wire is then introduced, typically through the puncturing needle or other introducer device into the lumen of the vessel. The introducer device is then removed, leaving the guide wire within the vessel. The guide wire projects beyond the surface of the skin. At this point, several options are available to a physician for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire, for example, for insertion of small diameter dual lumen catheters. If the catheter to be inserted is significantly larger than the guide wire, a dilator device is passed over the guide wire to enlarge the opening into the vessel and then removed. The catheter is then passed over the guide wire, and the guide wire is then removed, leaving the catheter within the vessel for withdrawing blood into the hemodialysis machine and returning dialysed blood to the patient.

During hemodialysis, the two lumens, the arterial lumen and the venous lumen, are connected to a hemodialysis machine and are used to remove toxic blood from the patient for dialysis and to return dialyzed blood to the patient, respectively. However, suction of the toxic blood into the arterial lumen may draw the distal opening of the arterial lumen against the wall of the blood vessel into which the lumen is inserted, reducing or cutting off blood flow through the arterial lumen, and significantly reducing the amount of blood being dialyzed. This reduction in blood flow can lead to longer dialysis period, or result in less dialysis of the patient's blood. It would be beneficial to provide a catheter that reduces the suction of the arterial lumen against the blood vessel wall.

Twardowski et al., U.S. Pat. No. 5,405,320 and Davey et al., U.S. Pat. No. 6,280,423 B1 both disclose dual lumen catheters with an arterial lumen that includes an overhanging lip or shield to reduce the suction of the arterial lumen against the blood vessel wall. Additionally, U.S. Pat. No. 6,991,625 discloses a dual lumen catheter with an arterial lumen that includes a tip section that is undercut along the venous lumen, thereby facilitating prevention of occlusion by the vessel wall.

It is desired to provide a dual lumen catheter for hemodialysis wherein the aspirating lumen is protected from inadvertent occlusion by the vessel wall.

BRIEF SUMMARY OF THE INVENTION

The present invention is a dual lumen catheter having an arterial lumen and a venous lumen with discrete, axially staggered distal tip openings, wherein the venous lumen distal tip extends a selected distance beyond the distal tip of the arterial lumen. The arterial lumen is provided with an opening such as a side opening as well as with several side port openings for withdrawing blood from the body. The venous lumen provides return flow of the blood into the vessel. In addition, the venous lumen distal tip portion includes a protective structure proximal of the distal tip opening that includes an enlarged proximal end that expands upon insertion of the catheter into the vessel to engage the vessel wall, and includes a plurality of openings therethrough to permit blood flow therethrough. The protective structure centers the distal tip portion of the venous lumen and also centers the distal tip portion of the arterial lumen within the vessel wall whereby the arterial distal tip opening is not sucked into occlusive engagement with the vessel wall which would diminish its efficiency in withdrawing blood from the vessel.

Preferably the protective structure is thin and of soft durometer and shaped like an umbrella, with a plurality of pleats that extend proximally from the connection of the protective structure with the venous lumen distal tip portion. Rounded proximal edge portions of the protective structure facilitate later removal of the catheter from the vessel.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
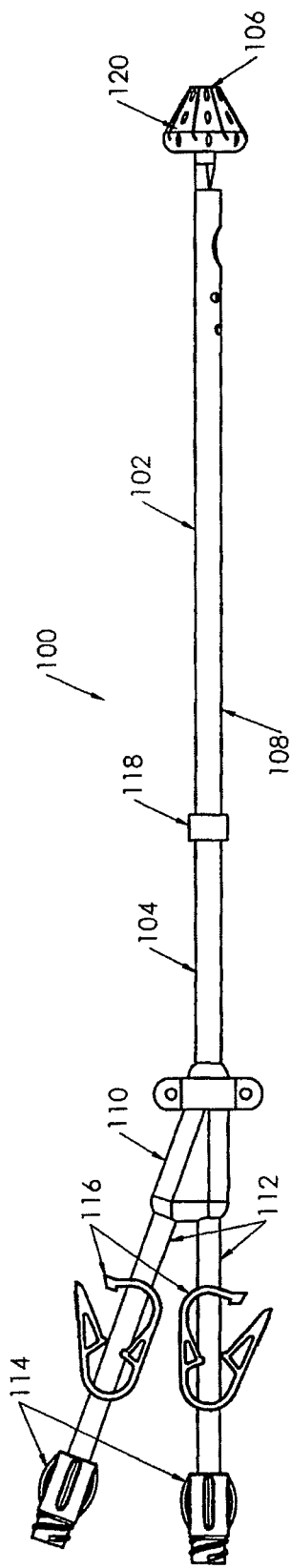
FIG. 1 is a side view of a dual lumen catheter containing the present invention.

In the drawings, like numerals indicate like elements throughout. Certain terminology is used herein for convenience only and is not to be taken as a limitation on the present invention. The terms "distal" and "proximal" refer to directions away from and closer to, respectively, the insertion tip of the catheter according to the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

In FIG. 1, a dual lumen catheter assembly 100 is illustrated that includes a catheter 102 having a proximal end 104, a distal end 106, and an elongated body 108 extending therebetween. Catheter 102 comprises first and second catheter lumens, one being known as a venous lumen for returning blood to the patient, and the other being known as an arterial lumen for withdrawing blood from the patient. While the catheter body 108 preferably has a generally circular cross section, the first and second lumens each may have a generally "D-shaped" cross section, juxtaposed from each other across a common sidewall. Alternatively, the lumens of the catheter could have a round or oval cross-sectional shape, and the two lumens could be attached side-by-side or be split apart at the distal end. It is preferred that the cross section of the body 108 be a generally smooth curve to facilitate sealing of the patient's skin around the body 108 at the incision site, as well as at the entrance to the vessel, to minimize bleeding.

A hub 110 is affixed onto the proximal end 104 of catheter 102, and preferably includes a suture wing that extends generally transverse of the body 108 and is shown to have two suture openings that allow an inserting physician to suture the hub 110 to the external skin of the patient into whom the physician has inserted the catheter assembly 100 to prevent the catheter assembly 100 from being dislodged from its inserted position within the patient.

Joined to the proximal ends of the first and second lumens of the catheter 102 are first and second extension tubes 112 that fluidly communicate respectively with the first and second lumens within conduits of hub 110. Proximal ends of the first and second extension tubes 112 preferably terminate at first and second connectors 114, such as standard luer locks, as is well known in the art. First and second clamps 116, such as a Roberts clamps, are preferably disposed over the first and second extension tubes 112 and serve to releasably close off each of the first and second extension tubes, respectively, preventing fluid flow through each of the first and second extension tubes 112 when the respective clamps are in the closed position.

Preferably, a catheter tissue ingrowth cuff 118 is disposed along an exterior of the body 108 between the distal tip 106 and the hub 110. The catheter tissue ingrowth cuff 118 is used for chronic catheter insertions, wherein the catheter assembly 100 is intended to be inserted into the patient for extended periods of time, such as for several months. The catheter tissue ingrowth cuff 118 is disposed within a subcutaneous tunnel according to methods known by those skilled in the art.

Figure 2:
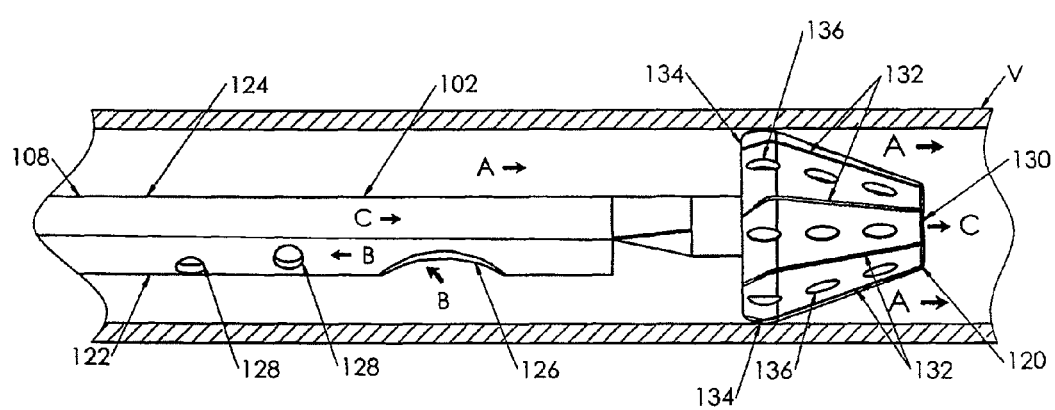
FIG. 2 is an enlarged side view of the distal portion of the catheter of FIG. 1 after insertion of the catheter into a vessel, with the protective structure expanded to engage the vessel walls, and the flow of the blood in the vessel and into and from the arterial and venous distal tip openings, respectively.
Figure 3:
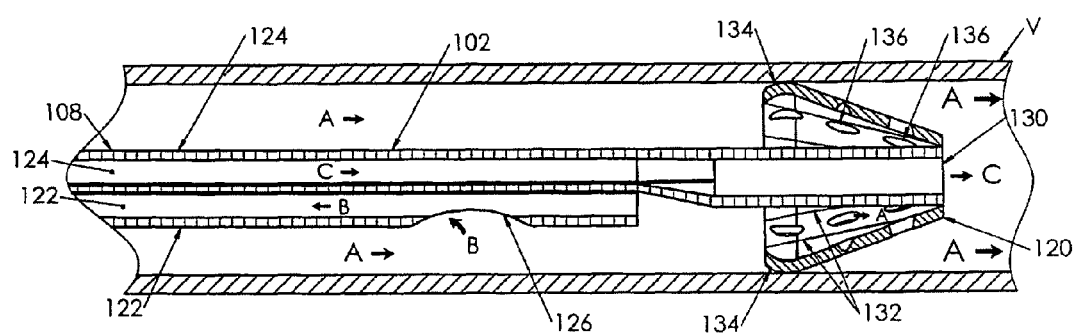
FIG. 3 is a cross-sectional view of the distal portion of the catheter of FIG. 2.

With respect to FIGS. 2 and 3, the present invention includes a distal tip protector 120 integrally defined on the distal tip 106 of catheter 102. In these figures, the distal portion of the catheter is shown in position inserted within a venous vessel V. Catheter 102 is shown to include first lumen 122 for withdrawal of fluids from venous vessel V, and second lumen 124 for returning blood that was withdrawn from the vessel to be returned to the vessel. The distal tip of second lumen 124 is located a distance distally of the distal tip of the first lumen, which minimizes any tendency of returned blood to be aspirated by the first lumen and which thus enhances the efficiency of the hemodialysis. Flow of blood generally within the vessel V is shown by directional arrow A. Flow of blood within first or arterial lumen 122 is shown by directional arrow B, with its intake occurring at first distal lumen opening 126 and preferably through one or more side ports 128; also, the distal tip of lumen 122 may be open. Flow of blood within second or venous lumen 124 is shown by directional arrow C, with flow exiting from the lumen into the vessel from second distal lumen opening 130 and being parallel to vessel blood flow A.

Figure 4:
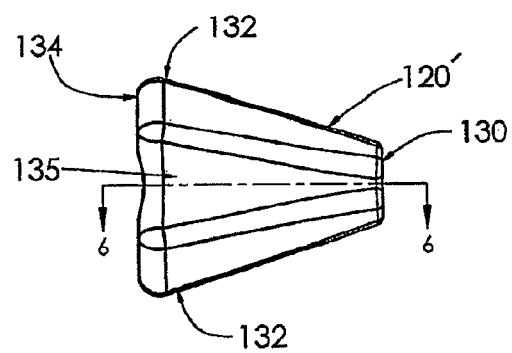
FIGS. 4 to 6 illustrate an alternate embodiment of the present invention.
Figure 5:
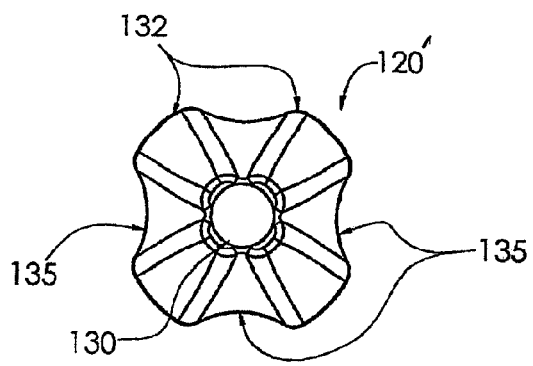
Figure 6:
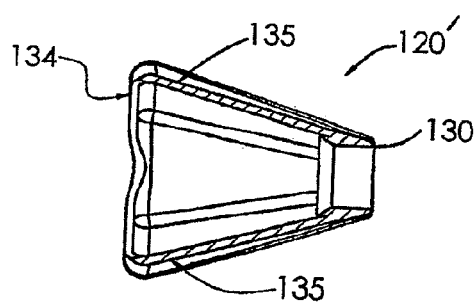

Distal tip protector 120 is generally shaped like an umbrella or mushroom and extends proximally from the distal tip and radially outwardly, and has numerous pleats or folds 132 that allow the protector 120 to be compressed for insertion into the vessel. Protector 120 also includes a generally rounded proximal or bottom edge 134 that allows the catheter to be eventually slid out of the vessel for removal. A plurality of through-openings 136 are defined on the protector serving as through-ways to allow blood flowing through the vessel past first distal opening 126. Pleats 132 define channels into the outer surface of protector 120; and, as best seen in FIGS. 4 to 6 in which an expanded protector 120' of an alternate embodiment is illustrated, channels 135 define through-ways to allow blood to continue flowing through and past the protector with little impediment, when protector 120' expands against the vessel wall.

First distal lumen opening 126 is shown to be directed laterally, not axially, to further lessen the tendency of aspiration of returned blood exiting from second distal lumen opening 130. However, such lateral orientation, without the protector 120 of the present invention, would make the opening susceptible to occlusion by the vessel wall. Protector 120, however, while being quite flexible to facilitate insertion and removal of the catheter into and from the patient, is sufficiently rigid for rounded bottom edge 134 to press against the vessel wall and to center the distal catheter portion within the vessel V thus preventing occlusion of first distal lumen opening 126.

Preferably, the body 108 is constructed from a polymer or elastomer, such as polyurethane or silicone, with a radiopaque filler material therein to aid in locating the body 108 within the patient's vessel after insertion, such as by ultrasound and fluoroscopy. However, those skilled in the art will recognize that other biocompatible materials may be used for the body 108. Preferably, the body 108 has a hardness of approximately 70-A to 80-A on the Shore durometer scale, although those skilled in the art will recognize that the body 108 may be harder or softer. The thickness of tip protector 120 could be in the range of from about 0.0010 in (0.254 mm) to about 0.0035 in (0.889 mm), and more preferably, from about 0.0015 in (0.381 mm) to about 0.0025 in (0.635 mm). If the material used is silicone elastomer, the thickness may be slightly thicker. Protector 120 could be molded integrally with catheter body 108, but it could be solvent bonded or fused thereto. Regarding holes 136, they may each have a size of about 0.01 in (2.54 mm) to about 0.10 in (25.4 mm), and more preferably from about 0.03 in (7.62 mm) to about 0.07 in (17.8 mm). All holes 136 should be relatively spaced away a slight distance from distal tip 130 and bottom edge 134 to preserve structural integrity, and be spaced apart from each other about 0.02 in (5.08 mm), for example. Openings 136 could have different diameters from each other, if desired; for example, the openings near to distal tip 130 could be smaller than those near rounded proximal or bottom edge 134. The openings could have rounded, oblong or oval or other shapes, as desired. The holes could also be aligned in four or five columns extending longitudinally along the axis of the lumen.

To insert the catheter assembly 100 into the patient, an incision is initially made near an insertion site on the patient's skin, which is to be aspirated with a syringe or other introducer apparatus near or proximate the area to be catheterized. If the catheter assembly 100 is used for hemodialysis and the area to be catheterized is the internal jugular vein, the incision is made in the supra-clavicular triangle region. The exact location of the incision can be varied by the physician. Initially, the proximal portion of the catheter would have been located within a subcutaneous tunnel in the subcutaneous area of the patient's torso, using one of various tunneling techniques. In one preferred technique, the distal end region of the catheter would have been pulled through the tunnel from a remote end of the tunnel, with the tunnel formed using a trocar or other tunneling tool, leaving the proximal end region at least partially within the tunnel, with the proximal end extending beyond the tunnel and exterior of the patient. In accordance with the Seldinger technique, a hollow needle is inserted through the incision and into the vein, and the vein is then aspirated. A guide wire is then passed through the needle and the needle is removed. Next, after dilating the soft tissue track and venatory site, the catheter assembly 100 is inserted over the guide wire. This insertion technique eliminates the need for a sheath to be inserted over the guide wire, greatly reducing the risk of air embolism.

In use, after the dialysis machine is connected to the catheter assembly 100 and turned on, the dialysis machine draws blood from the vessel through the first lumen 122. In the event that the pressure drop in the vessel caused by the blood being drawn into the first lumen 122 forces the wall of the vessel toward the first distal opening 126, the protector 120 prevents the vessel wall from totally occluding the first distal opening 126 and shutting off blood flow through the first lumen 122.

The blood drawn into the first lumen 122 flows to the hemodialysis machine where the blood is cleaned and processed. The blood is then pumped through the second lumen 124 for discharge back into the vessel through second distal opening 130 and side holes 136.

In FIGS. 4 to 6 another embodiment of the protected distal tip of the present invention is illustrated. The protector 120' is shown to have a pleated design and have a plurality of through-ways or channels 135 defined into and axially along the outer surface thereof extending distally from the proximal end 134 thereof, through which blood may flow therepast when the protected distal tip is positioned within a blood vessel in a manner similar to that shown in FIG. 2.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A multilumen catheter assembly for use in hemodialysis and implantable into the vasculature of a patient, comprising:
   an elongated body, having a proximal end and a distal end, defining a first lumen having a sidewall extending between the proximal end and a first lumen distal end proximate the body distal end and a first distal opening disposed proximate the first lumen distal end and defining a first blood flow port communicable with a surrounding environment, and a second lumen connected to the sidewall and extending between the proximal end and a second lumen distal end proximate the body distal end, the second lumen distal end distal of the first lumen distal end, wherein the second lumen includes a second distal opening disposed distally of the first distal opening and defining a second blood flow port communicable with a surrounding environment; and
   a self-expanding protector adjoining the elongate body distally of the first distal opening, the protector extending from an inner edge, positioned circumferentially about the second lumen distal end such that the inner edge and a distal tip of the second lumen distal end are coterminous, radially outwardly and proximally to a free proximal edge that extends circumferentially about the elongate body proximate the second distal opening, the protector defining through-ways that permit blood flow past the protector.

2. The assembly of claim 1, wherein the protector is pleated and is adapted to be compressed radially toward the elongate body during catheter insertion and removal.

3. The assembly of claim 1, wherein the protector free proximal edge is rounded and continuous to facilitate being slid along the vessel wall during insertion and removal of the catheter into and from the vessel.

4. The assembly of claim 1, wherein the through-ways are defined by a plurality of openings extending through a body portion of the protector between the inner edge and the free proximal edge.

5. The assembly of claim 4, wherein the openings have diameters of from about 0.01 in to about 0.10 in.

6. The assembly of claim 4, wherein the openings have diameters of from about 0.03 in to about 0.07 in.

7. The assembly of claim 4, wherein the openings are spaced from the free proximal edge and the inner edge.

8. The assembly of claim 1, wherein the first distal opening opens laterally of the catheter.

9. The assembly of claim 1, wherein the first lumen includes at least one side port proximate the first distal opening.

10. The assembly of claim 1, wherein the second lumen, distally of the first lumen distal tip section, includes a transition portion that transitions the cross-section of the second lumen from a generally noncircular cross section shape to a generally circular cross section shape.

11. The assembly of claim 1, wherein the protector has a thickness of from about 0.0010 in to about 0.0035 in.

12. The assembly of claim 1, wherein the protector has a thickness of from about 0.0015 in to about 0.0025 in.

13. The assembly of claim 1, wherein the protector has an umbrella shape.

14. The assembly of claim 1, wherein the protector has a hardness of approximately 70-A to 80-A Shore durometer.

15. The assembly of claim 1, wherein the protector is of silicone elastomer.

16. The assembly of claim 1, wherein the protector is integrally joined to the elongate body.

17. The assembly of claim 1, wherein through-ways include a plurality of pleat folds defined along an outer surface of the protector and extending through the proximal free end of the protector.

18. The assembly of claim 1, wherein through-ways include a plurality of channels defined along an outer surface of the protector and extending through the proximal free end of the protector.

19. The assembly of claim 1, wherein the protector is biased radially outward.

20. The assembly of claim 1, wherein the protector is configured to engage blood flowing thereby to assist in self expansion.

* * * * *